(12) United States Patent
Liu et al.

(10) Patent No.: US 10,960,140 B2
(45) Date of Patent: Mar. 30, 2021

(54) MINI SYRINGE

(71) Applicant: YOMURA TECHNOLOGIES INC., New Taipei (TW)

(72) Inventors: Liang-Chuan Liu, New Taipei (TW); Shih-Wei Li, New Taipei (TW)

(73) Assignee: Yomura Technologies Inc., New Taipei (TW)

( * ) Notice: Subject to any disclaimer, the term of this patent is extended or adjusted under 35 U.S.C. 154(b) by 252 days.

(21) Appl. No.: 16/134,146

(22) Filed: Sep. 18, 2018

(65) Prior Publication Data

US 2020/0086058 A1     Mar. 19, 2020

(51) Int. Cl.
*A61M 5/315*     (2006.01)
*A61M 5/32*     (2006.01)

(52) U.S. Cl.
CPC .... *A61M 5/31556* (2013.01); *A61M 5/31555* (2013.01); *A61M 5/329* (2013.01); *A61M 2207/00* (2013.01)

(58) Field of Classification Search
CPC .......... A61M 2207/00; A61M 5/31555; A61M 5/31556; A61M 5/329; A61M 5/34; A61M 5/347; A61M 5/348; A61M 39/00; A61M 39/02; A61M 39/10; A61M 2039/1033; A61M 2039/1038; A61M 39/105; A61M 39/1055

See application file for complete search history.

(56) References Cited

U.S. PATENT DOCUMENTS

| | | | |
|---|---|---|---|
| 2004/0111066 A1* | 6/2004 | Prais | B24B 19/16 604/239 |
| 2009/0008393 A1* | 1/2009 | Howlett | A61M 39/162 220/380 |
| 2015/0105749 A1* | 4/2015 | Laugere | A61M 5/19 604/506 |

\* cited by examiner

*Primary Examiner* — Quynh-Nhu H. Vu
(74) *Attorney, Agent, or Firm* — Rosenberg, Klein & Lee

(57) ABSTRACT

A mini syringe includes a tubular base member, a microneedle unit including a microneedle device and a compressible pharmacy housing device and mounted in the bottom side of the base member, a plunger mounted in the base member and pressable to compress the pharmacy housing device, and an adjustment cover threaded onto the base member for controlling the moving distance of the plunger in a micro-adjustable manner.

11 Claims, 4 Drawing Sheets

MINI SYRINGE

BACKGROUND OF THE INVENTION

1. Field of the Invention

The present invention relates to syringe technology, and more particularly to a mini syringe, which has a small size and is practical for quantitative injection in a convenient manner.

2. Description of the Related Art

Due to the prosperity of industry and commerce, people are struggling with life, which affects their health. Further, due to improper diet, the number of people with chronic diseases is high. Patients with chronic diseases need daily injections for treatment and disease control. Whether it is a chronic disease patient or a general patient, most of the traditional injection needles are used for injection treatment. The needle diameter of a traditional injection needle is about 1 mm and the needle length is about 1-3 cm. Therefore, the injection will penetrate deep into the subcutaneous tissue and cause pain, so the traditional injection needle not only brings pain to the patient, but the injected needle hole is more likely to increase the risk of infection.

Therefore, some manufacturers have developed microneedle syringes. A micro-needle syringe uses a conventional syringe barrel to hold a needle holder with a large number of micro-needles. The use of a conventional syringe barrel cannot accurately control the dosage. It is only suitable for general injection by medical staff, not suitable for carrying out, self-injection or quantitative drug injection.

SUMMARY OF THE INVENTION

The present invention has been accomplished under the circumstances in view. It is therefore the main object of the present invention to provide a mini syringe, which has at least one pharmacy chamber for accurately filling the dosage for quantitative injection.

It is another object of the present invention to provide a mini syringe, which has at least one pharmacy chamber for accurately filling the dosage and a convenient and safe structural design. It is disposable for one single use and does not require professional medical personnel to perform injection.

To achieve these and other objects of the present invention, a mini syringe comprises a microneedle unit, a base member, a plunger, an adjustment cover and a spacer ring. The base member comprises a center hole, a flange extended around a bottom side thereof, and an outer thread spirally extended around the periphery thereof. The microneedle unit is mounted in the bottom end of the center hole of the base member and consists of a microneedle device and a pharmacy housing device. The microneedle device comprises at least one microneedle. The pharmacy housing device comprises at least one drug chamber respectively disposed corresponding to the at least one microneedle. The plunger is mounted in the opposing top end of the center hole of the base member, comprising a plunger body axially slidably inserted into the center hole of the base member, a reduced outer diameter portion upwardly extended from the top side of the plunger body and at least one plunger tip aimed at the at least one drug chamber. The adjustment cover comprises an inner thread threaded onto the outer thread of the base member, and a through hole for the passing of the reduced outer diameter portion of the plunger. The spacer ring is mounted between the bottom side of the adjustment cover and the flange of the base member. Further, the microneedle device comprises a base panel and at least one microneedle. Further, the pharmacy housing device comprises at least one drug chamber corresponding to said at least one microneedle. Further, the plunger body of the plunger body fits the center hole of the base member and is axially movable relative to the base member by a thrust. Preferably, the spacer ring is made of silicone rubber for fine adjustment of the axial displacement of the plunger by the adjustment cover. Preferably, the pharmacy housing device is made of silicone rubber by molding. Preferably, the base panel and said at least one microneedle of the microneedle device are selectively made of 304 or 316 series stainless steel. Preferably, each microneedle is about 1.3-2.0 mm high, 0.2-0.7 mm outer diameter, 0.1-0.5 mm inner diameter, and 0.05-0.15 mm wall thickness. Preferably, the base panel and at least one microneedle of the microneedle device are selectively formed by deep drawing of sheet metal, metal electroforming, stamping or 3D printing.

DETAILED DESCRIPTION OF THE PREFERRED EMBODIMENT

Figure 1:
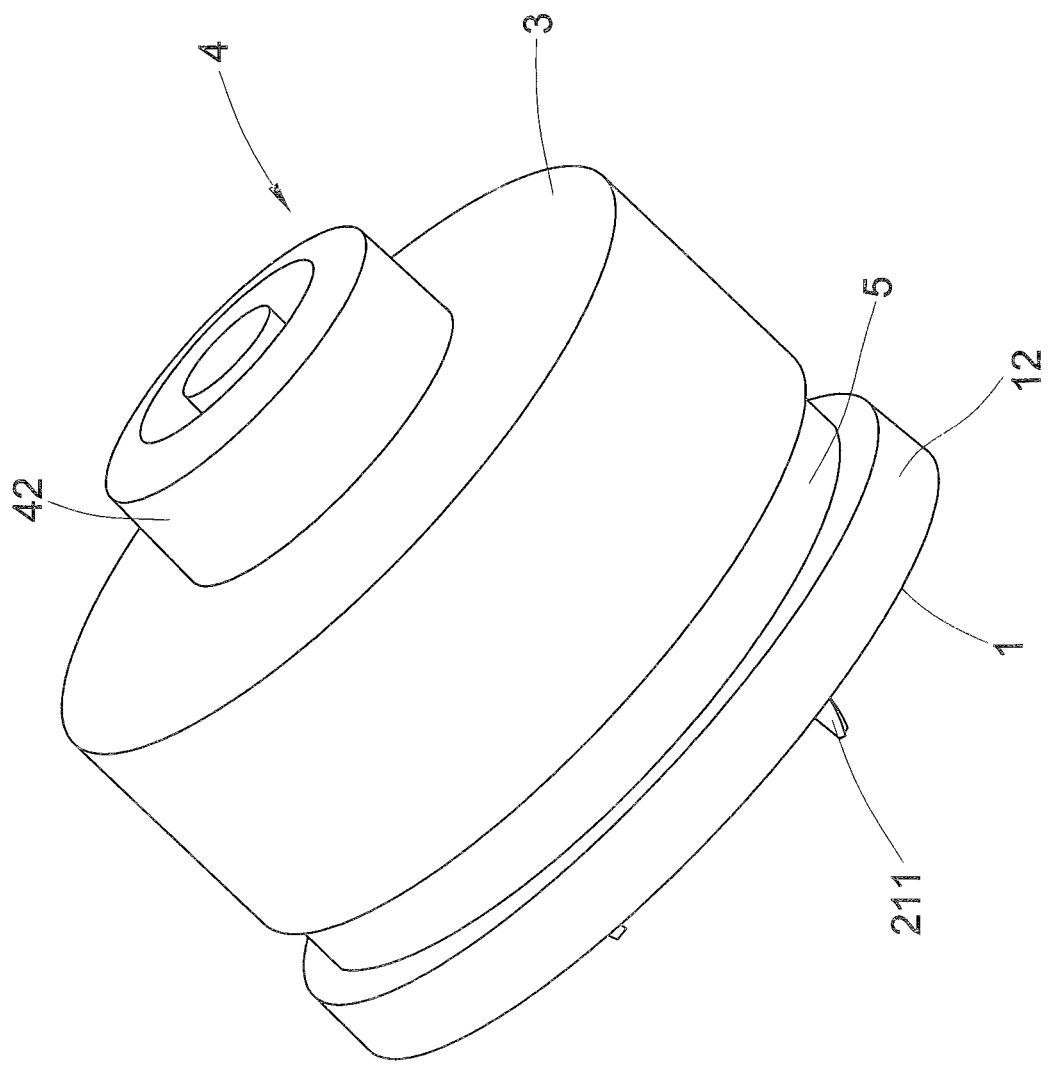
FIG. 1 is an oblique top elevational view of a mini syringe in accordance with the present invention.
Figure 2:
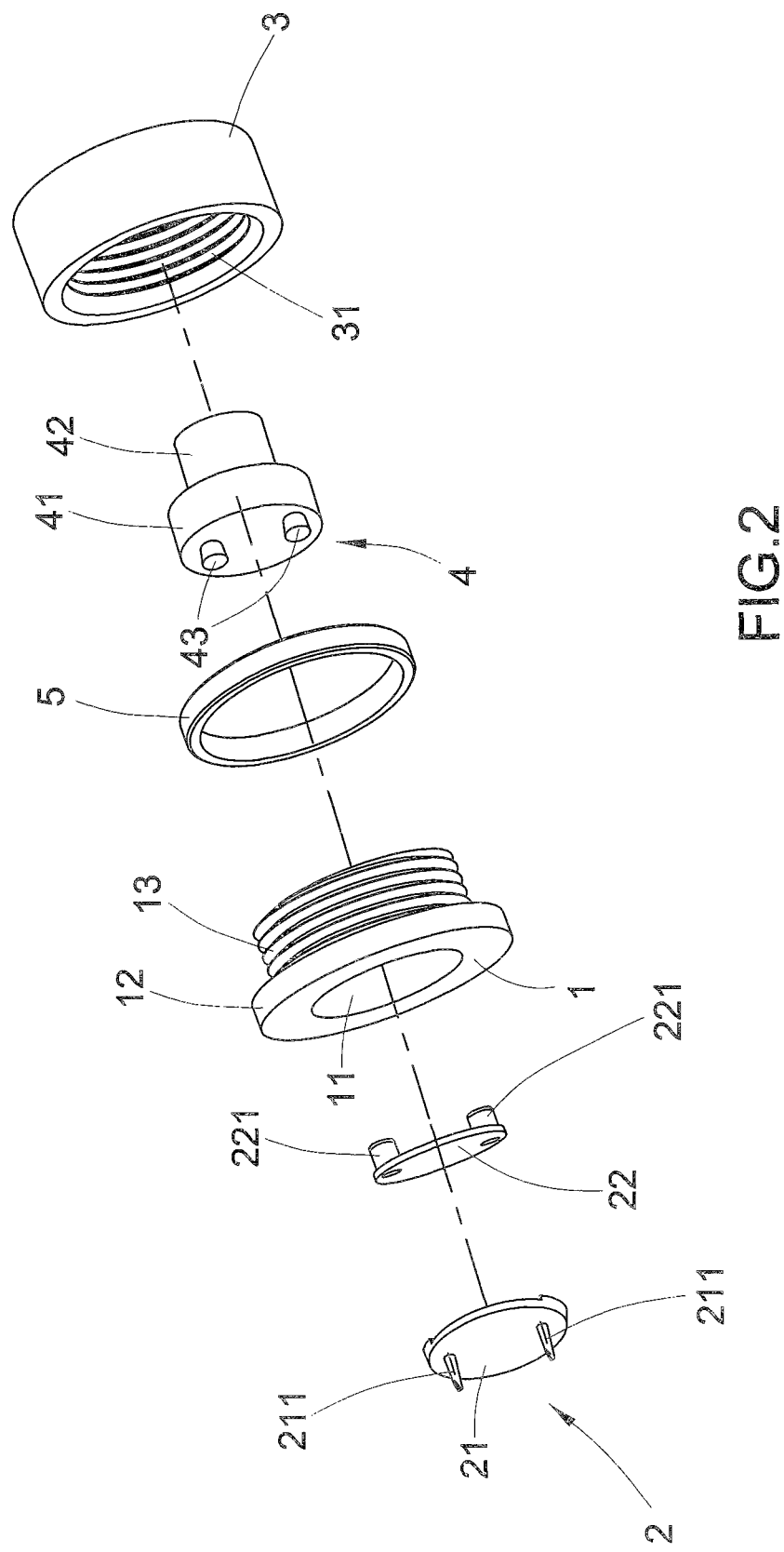
FIG. 2 is an exploded view of the mini syringe in accordance with the present invention.
Figure 3:
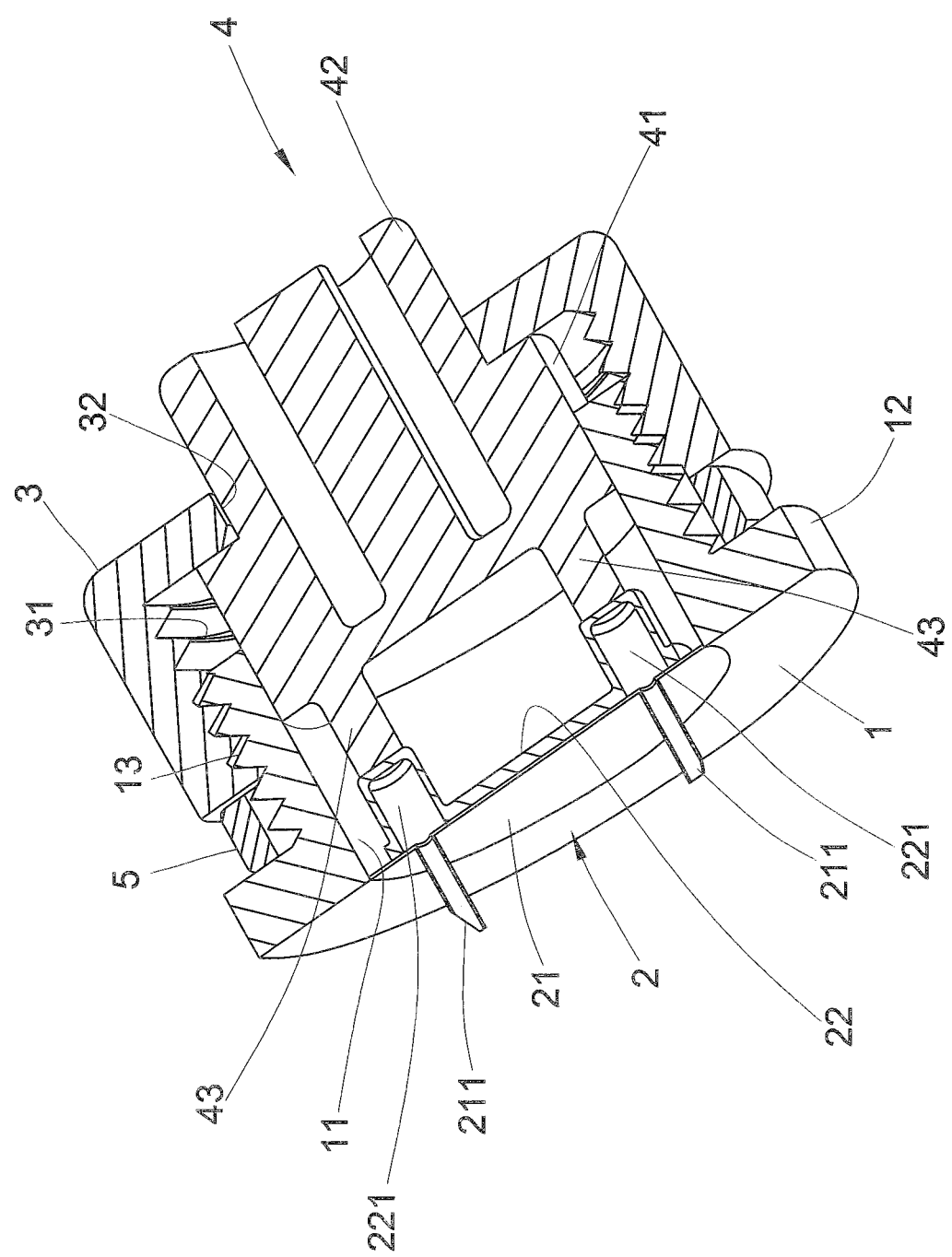
FIG. 3 is a sectional elevation of the mini syringe in accordance with the present invention.
Figure 4:
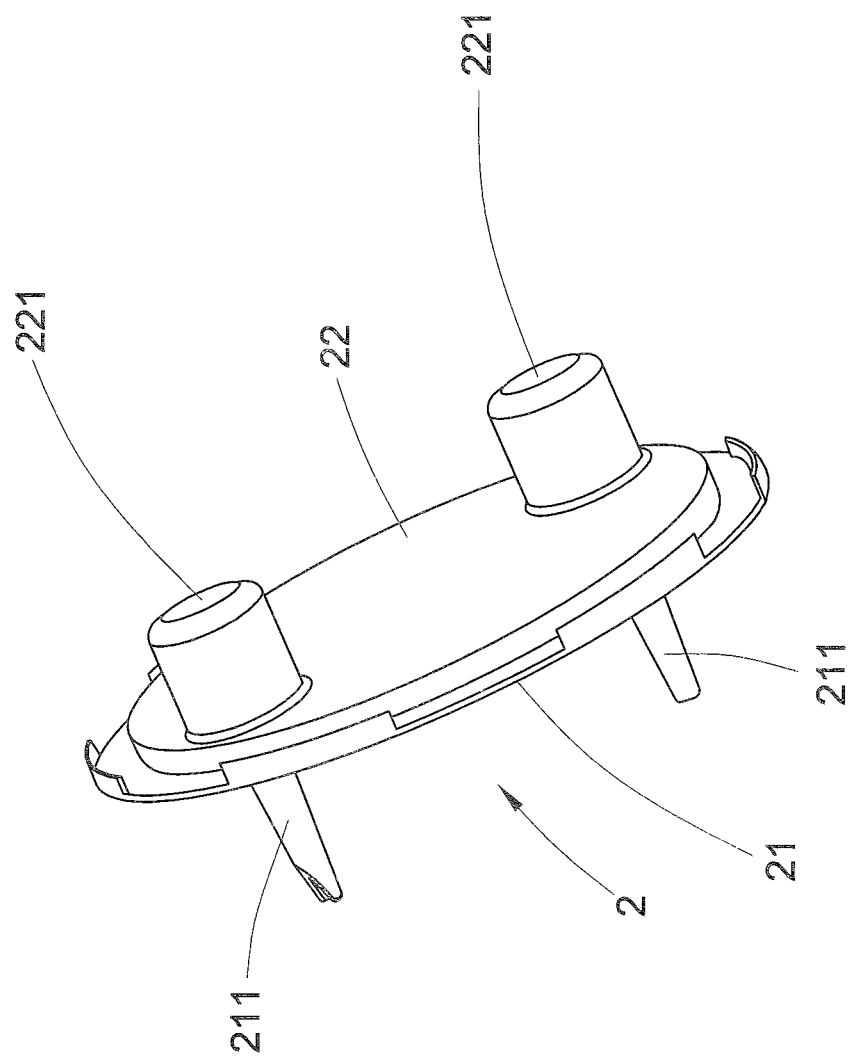
FIG. 4 is an oblique top elevational view of the microneedle unit of the mini syringe in accordance with the present invention.

Referring to FIGS. 1-4, a mini syringe in accordance with the present invention is shown. The mini syringe comprises a microneedle unit, a base member (1), a plunger (4), an adjustment cover (3) and a spacer ring (5). The base member (1) is a tubular member, comprising a center hole (11), a flange (12) extended around a bottom side thereof, and an outer thread (13) spirally extended around the periphery thereof. The microneedle unit is mounted in a bottom side of the center hole (11) of the base member (1), consisting of a microneedle device (2) and a pharmacy housing device (22). The microneedle device (2) comprises at least one microneedle (211). The pharmacy housing device (22) comprises at least one drug chamber (221) respectively disposed corresponding to the at least one microneedle (211). The plunger (4) is mounted in the opposite top end of the center hole (11) of the base member (1), comprising a reduced outer diameter portion (42) at a top side thereof. The adjustment cover (3) comprises an inner thread (31) threaded onto the outer thread (13) of the base member (1), and a through hole (32) for the passing of the reduced outer diameter portion (42) of the plunger (4). The spacer ring (5) is mounted between the bottom side of the adjustment cover (3) and the flange (12) of the base member (1). As the adjustment cover (3) and the base member (1) are threaded together, the spacer ring (5) limits the locking position of the adjustment cover (3), so that when the adjustment cover (3) is fastened tight, the at least one plunger tip (43) of the plunger (4) is moved into contact with the top edge of the at least one drug chamber (221) of the pharmacy housing device (22) and the plunger body (41) of the plunger (4) fits the center hole (11) of the base member (1) in a slightly tight manner. At this time, the plunger (4) needs to be axially moved by a certain thrust. Further, the spacer ring (5) is made of silicone rubber with appropriate compression for fine adjustment of the axial displacement of the plunger (4) by the adjustment cover (3). The pharmacy housing device (22) is made of silicone rubber by molding. The microneedle device (2) comprises a base panel (21) and at least one microneedle (211). The microneedle device (2) is made of 304 or 316 series stainless steel. The microneedle (211) is about 1.3-2.0 mm high, 0.2-0.7 mm outer diameter, 0.1-0.5 mm inner diameter, and 0.05-0.15 mm wall thickness.

The base panel (21) and microneedle (211) of the microneedle device (2) can be formed by deep drawing of sheet metal, metal electroforming, stamping or 3D printing.

When using the mini syringe, pressing the plunger (4) downwards will cause the at least one plunger tip (43) to squeeze the at least one drug chamber (221) of the pharmacy housing device (22), forcing the liquid medicine out of the at least one drug chamber (221) and the at least one microneedle (211) for painless injection in a safe manner.

In summary, the mini syringe of the present invention has at least one pharmacy chamber for accurately filling the dosage and a convenient and safe structural design. It is disposable for one single use and does not require professional medical personnel to perform injection.

What the invention claimed is:

1. A mini syringe, comprising:
   a base member defining a center hole having opposing top and bottom ends, said base member including:
      a flange extended around said bottom end of said center hole, and
      an outer thread spirally extended around a periphery of said base member;
   a microneedle unit mounted at said bottom end of said center hole of said base member, said microneedle unit including:
      a microneedle device including at least one microneedle, and
      a pharmacy housing device including at least one drug chamber respectively disposed corresponding to said at least one microneedle;
   a plunger mounted in said center hole of said base member and protruding from said top end of said center hole, said plunger including:
      a plunger body having opposing top and bottom sides, said plunger body being axially slidable within said center hole of said base member between first and second positions,
      a reduced outer diameter portion extending from said top side of said plunger body, and
      at least one plunger tip protruding from said bottom side of said plunger body toward said at least one drug chamber of said pharmacy housing device for compressing said at least one drug chamber responsive to displacement of said plunger body to said first position;
   an adjustment cover including an inner thread threaded onto said outer thread of said base member and defining a through hole configured for passing said reduced outer diameter portion of said plunger therethrough; and
   a spacer ring mounted between a bottom side of said adjustment cover and said flange of said base member.

2. The mini syringe as claimed in claim 1, wherein said microneedle device further includes a base panel.

3. The mini syringe as claimed in claim 2, wherein said base panel and said at least one microneedle of said microneedle device are selectively formed by deep drawing of sheet metal, metal electroforming, stamping or 3D printing.

4. The mini syringe as claimed in claim 1, wherein said plunger body of said plunger is axially slidable within said center hole relative to said base member by a thrust applied to said reduced outer diameter portion.

5. The mini syringe as claimed in claim 1, wherein said spacer ring is made of silicone rubber for fine adjustment of a range of axial displacement of said plunger body by said adjustment cover.

6. The mini syringe as claimed in claim 1, wherein said pharmacy housing device is made of silicone rubber by molding.

7. The mini syringe as claimed in claim 2, wherein said base panel and said at least one microneedle of said microneedle device are selectively made of 304 or 316 series stainless steel.

8. The mini syringe as claimed in claim 1, wherein said at least one microneedle is about 1.3-2.0 mm high, 0.2-0.7 mm outer diameter, 0.1-0.5 mm inner diameter, and 0.05-0.15 mm wall thickness.

9. The mini syringe as claimed in claim 1, wherein said through hole of said adjustment cover has a diameter wider than a diameter of said reduced outer diameter portion of said plunger and narrower than a diameter of said plunger body of said plunger.

10. The mini syringe as claimed in claim 1, wherein said adjustment cover and said pharmacy housing device collectively restrict axial displacement of said plunger body to between said first and second positions.

11. The mini syringe as claimed in claim 1, wherein said at least one plunger tip is in contact with a top edge of said at least one drug chamber when said plunger body is at said second position.

* * * * *